United States Patent [19]

Melech

[11] Patent Number: 5,193,563
[45] Date of Patent: Mar. 16, 1993

[54] SURGICAL SUITE SCRUB STATION

[76] Inventor: Victor P. Melech, Suite 1004, 12141 Jasper Avenue, Edmonton, Alberta, Canada, T5N 3X7

[21] Appl. No.: 691,845

[22] Filed: Apr. 26, 1991

[30] Foreign Application Priority Data

Apr. 30, 1990 [GB] United Kingdom ............... 9009669

[51] Int. Cl.⁵ .............................................. B08B 3/02
[52] U.S. Cl. ............................. 134/100.1; 134/103.1; 134/103.2; 134/199; 134/200
[58] Field of Search ................. 134/57 R, 100, 101, 134/113, 199, 200, 100.1, 103.1, 103.2; 340/825.31, 825.34; 222/52, 325

[56] References Cited

U.S. PATENT DOCUMENTS

| | | |
|---|---|---|
| 2,797,131 | 6/1957 | Parkes . |
| 3,039,699 | 6/1962 | Allen . |
| 3,589,378 | 6/1971 | Swanson et al. ............. 134/100 X |
| 3,699,984 | 10/1972 | Davis ............................ 134/95 |
| 3,757,806 | 9/1973 | Bhaskar et al. ............... 134/191 |
| 3,844,278 | 10/1974 | Weider . |
| 3,870,039 | 3/1975 | Moret et al. . |
| 3,918,987 | 11/1975 | Kopfer ........................... 134/95 |
| 4,020,856 | 5/1977 | Masterson . |
| 4,219,367 | 8/1980 | Cary, Jr. et al. ............... 134/29 |
| 4,332,264 | 6/1982 | Gortz et al. ................... 134/57 R |
| 4,465,522 | 8/1984 | Taldo et al. ................... 134/10 |
| 4,496,519 | 1/1985 | McGuire ....................... 376/316 |
| 4,670,010 | 6/1987 | Dragone ....................... 604/289 |
| 4,802,508 | 2/1989 | Styles et al. .................. 137/624.13 |
| 4,817,651 | 4/1989 | Crisp et al. ................... 134/102 |
| 5,031,797 | 7/1991 | Boris et al. ................... 222/52 X |

FOREIGN PATENT DOCUMENTS 2614518  11/1988  France ........................ 222/325

*Primary Examiner*—Philip R. Coe
*Attorney, Agent, or Firm*—Stevens, Davis, Miller & Mosher

[57] ABSTRACT

A surgical suite scrub station is disclosed provided with means to adjust the spacing between the forearm ports of the device from the ground on which the user stands during the use. Only a small amount of the cleansing mixture is recirculated to improve the ambient conditions by reducing the volume of gases normally generated when working with antimicrobial substances. An air curtain is used in preventing escape of cleansing or rinsing substance out of the forearm inserting ports of the cleansing compartment. The device presents improvement in convenience and economy of operation of surgical scrub stations.

4 Claims, 2 Drawing Sheets

SURGICAL SUITE SCRUB STATION

BACKGROUND OF THE INVENTION

The present invention relates to a hand and forearm cleansing device, particularly to a device used in surgical suites as a scrub station.

It is known that it is extremely important that the hands and forearms of a surgeon and of any personnel involved in surgery be thoroughly scrubbed and free of microbes. Many devices are known which serve this particular purpose. Briefly, they include cleansing mixture preparation means and an elongated cleansing compartment in which the scrubbing and rinsing of the forearms takes place. Within the cleansing compartment is disposed a set of cleansing mixture nozzles, stationary or rotary. The nozzles are directed radially inwardly towards the forearms and hands placed in the cleansing compartment.

U.S. Patent to Crisp et al. No. 4,817,651 depicts a typical example of a device of this kind. In this particular arrangement, a pair of rotary cleansing compartments is provided in which pulsating stream is directed towards the hands and forearms of the person utilizing the device.

U.S. Pat. No. 4,465,522 issued to Taldo et al. depicts another arrangement in which a manifold is arranged in an elongated compartment and is provided with means for controlling the pulsating of the scrubbing and rinsing liquid such as to avoid excessive noise encountered in previously known devices.

The known devices of this type have several disadvantages. First of all, they are not adapted to different height of the persons using the device with the resulting difference in the angle at which the forearms and hands of the person using the device are inserted into the cleansing compartments. This may result in an inappropriate cleansing not to mention the inconvenience for the user. Another drawback of the known devices is that, despite different curtains, boots or the like devices, a substantial amount of the liquid used in cleansing escapes out of the device through the ports in which the forearms of the person using the device are inserted.

Last but not least, the existing devices of this kind consume relatively large amounts of water and of the cleansing anti-microbial mixture. The known devices are not protected from operation with an unsuitable anti-microbial substance.

It is an object of the present invention to further advance the art of the devices described.

SUMMARY OF THE INVENTION

In general terms, the present invention provides hand and forearm cleansing device comprising, in combination: cleansing mixture preparation means; an elongated cleansing compartment for scrubbing and rinsing forearms and hands of a person; cleansing mixture spray means disposed in said cleansing compartment; conduit means hydraulically communicating said cleansing mixture preparation means with said spray means; height adjustment drive means for selectively modifying vertical distance between said cleansing compartment and the standing ground of the person.

In accordance with one feature, the port of the cleansing compartment for each hand is provided with a series of circumferentially, disposed nozzles directed radially inwardly and into the compartment to prevent liquid from dripping out of the compartment onto the floor. The nozzles are preferably arranged on a horizontally elongated locus, for each of the arms. According to another feature, the cleansing mixture is prepared in a relatively small amount which is recirculated within the device until such time as the specific cleansing operation is concluded whereupon it is drained and replenished with a fresh mixture.

In accordance with another feature of the invention, the anti-microbial mixture is supplied by means of a, preferably, sealed cartridge containing the substance and coded such that it cannot be substituted by another cartridge which would not have the particular code, be it a magnetic strip on a container or the shape of a cartridge or any other suitable means preventing a wrong container to be used for the purpose.

BRIEF DESCRIPTION OF THE DRAWINGS

The invention will now be described in greater detail with reference to the accompanying diagrammatic, simplified drawings wherein.

DETAILED DESCRIPTION OF THE PREFERRED EMBODIMENTS

Figure 1:
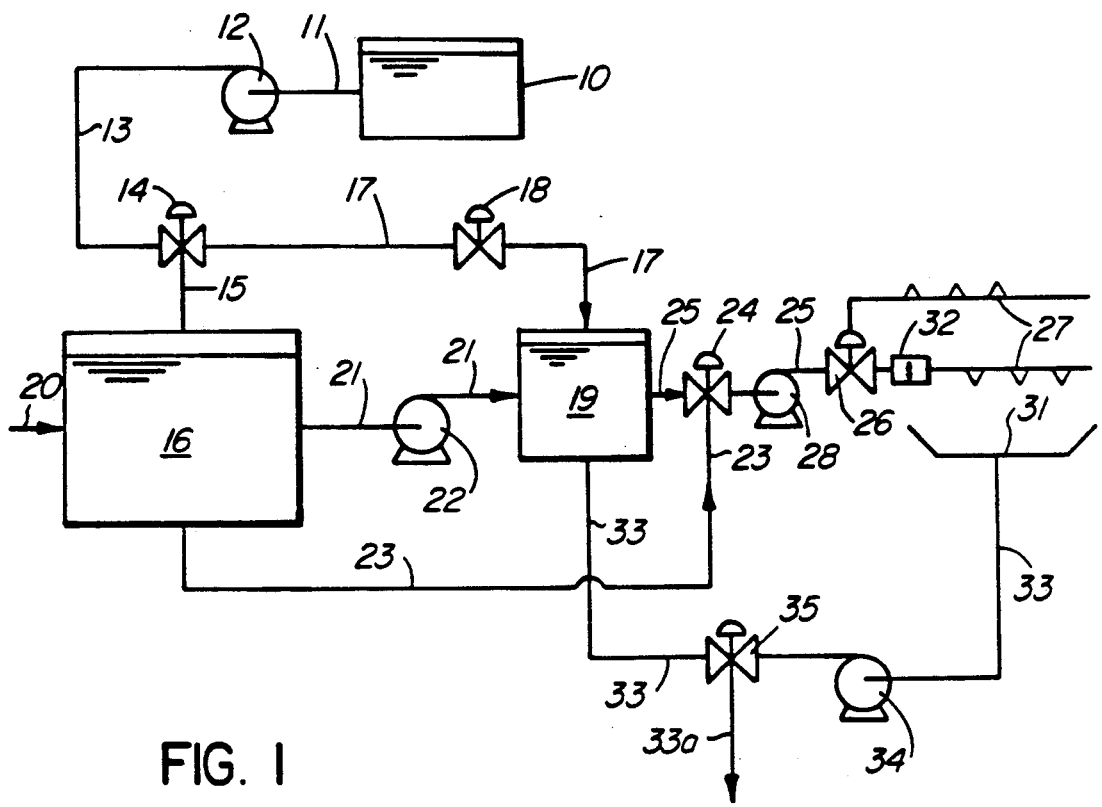
FIG. 1 is a simplified diagram of an exemplary embodiment of the device according to the present invention as originally considered, with certain parts not forming the invention omitted.

In FIG. 1, reference numeral 10 designates a coded anti-microbial cartridge/reservoir. The particular arrangement of the coding is not shown. It will suffice to say that the reservoir could be, for instance, a container provided with an encoded magnetic strip and with means allowing the bottle to be placed into the device only in such way that the coded strip faces a sensor, with the sensor allowing or disallowing the operation of the device depending whether the strip contains the required code or not. The coded reservoir 10 communicates through a conduit 11 with suction side of a metering pump 12 whose pressure side, in turn, communicates, via line 13 with a first anti-microbial valve 14. The anti-microbial valve 14 and many other components shown are operated by a control arrangement which is known in itself and have many different configurations or arrangements. Such control circuit is therefore not shown. It will suffice to say that the valve 14 is capable of alternately closing line 13, connecting it to a line 15 leading to a pre-heat reservoir 16 or connecting line 13 to a line 17 leading to an optional second valve 18. The second anti-microbial valve 18 is disposed in line 17. The downstream end of line 17 is in hydraulic communication with a recirculation tank 19. In the embodiment shown, the anti-microbial cartridge 10 has the capacity of about 9.5 liters and the recirculating reservoir has a capacity of about 11 liters. The pre-heat reservoir 10 accommodate approximately 38 liters of water supplied by a cold water inlet 20 provided with suitable valve or valves not shown in the drawings. The preheat reservoir 16 communicates with an upstream end of a water supply line 21 provided with a reservoir pump 22.

In the embodiment shown, a bypass line 23 bypasses the recirculation tank 19 to hydraulically communicate tank 16 directly with a recirculation/rinse valve 24. The valve 24 is disposed in a recirculation line 25 whose upstream end is hydraulically connected to the tank 19, the downstream end being connected to a distributor valve 26 operatively connected with a series of manifolds 27, a recirculation/rinse pump 28 is disposed in line 25 downstream of the valve 24. The manifolds are located inside cleansing compartments 29, 30 as is well known. Also arranged within the compartment or compartments 29, 30 is a collector sump 31. Throughout the present specification, the collector sump means is also alternatively referred to as a catch basin or as a "sump/recirculation tank", the terms designating the same element and being interchangeable. Since in the particularly preferred embodiments the basin also serves the purpose of mixing fresh water with the antimicrobial chemicals, the also forms a part of what is generally referred to as "cleansing mixture preparation means". A suitable source of vibrations, for instance an mechanical vibrator 32 is connected to the system of manifolds 27 and is adapted to vibrate same at a high frequency, in the general direction of stream of the jets flowing from the nozzles provided in the manifold.

The collector sump 31 communicates hydraulically with a recirculation line 33 provided with a drain/recirculation pump 34 and with a drain/recirculation valve 35 one of the ports of which is hydraulically connected with a drain line 33a.

Figure 2:
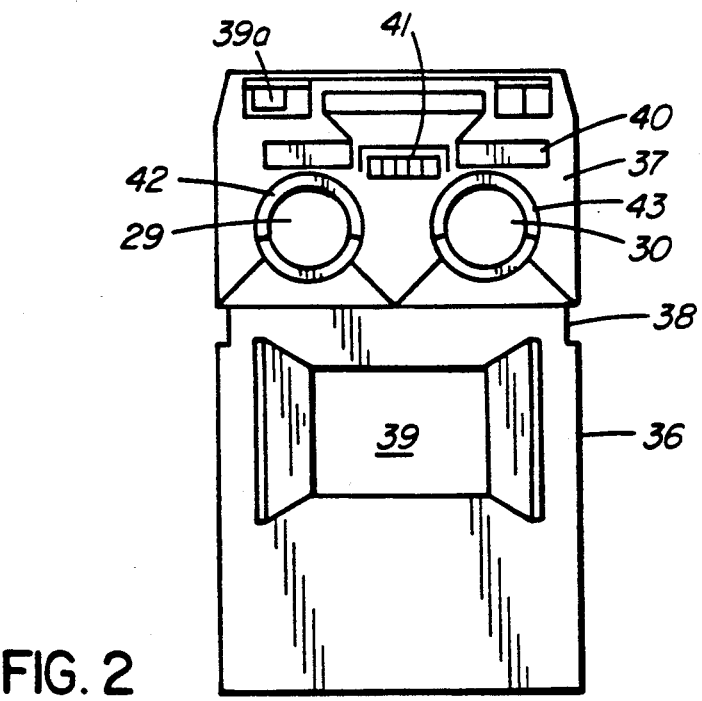
FIG. 2 is a simplified diagrammatic front view of the device of the present invention including a preferred way of securing the height adjustment of the cleansing compartments to suit persons of different height.

Turning now to FIG. 2, the device is shown as comprising two separate modules, a base module, also referred to as mechanical module 36 and a scrub module 37 disposed on top of the mechanical module 36. According to one of the features of the present invention and according to the embodiment shown, the upper scrub module 37 is telescopically mounted on the mechanical module 36 at 38 for vertical displacement to the extent of approximately 12 inches (about 30 centimeters). Reference numeral 39 designates an access opening for inserting the anti-microbial cartridge 10 into the mechanical module 36. The mechanical module 36 houses all components of FIG. 1 except for the manifolds 27, vibrator 21 and the collector pan or sump 31. A part of the respective conduits such as 25 and 33, of course, are also within the module 36. They are typically flexible hoses with anti-expansion cords. The front panel of the scrub module contains various control and indicating devices such as a readout panel 39a, activation switches 40, height adjustment switch pad 41 and other controls which are known per se and are therefore not shown in detail. The ports 29 and 30 contain each an air collar 42, 43. Each air collar is basically a ring-shaped, hollow, stationary ring connected to a suitable source of pressurized, cleansed microbe-free air. The ring has a plurality of nozzles which are directed toward the center of each port and inwardly of the respective compartment to prevent escape of liquid deposited onto hands and forearms of the user during the cleansing or rinsing operation.

Figure 3:
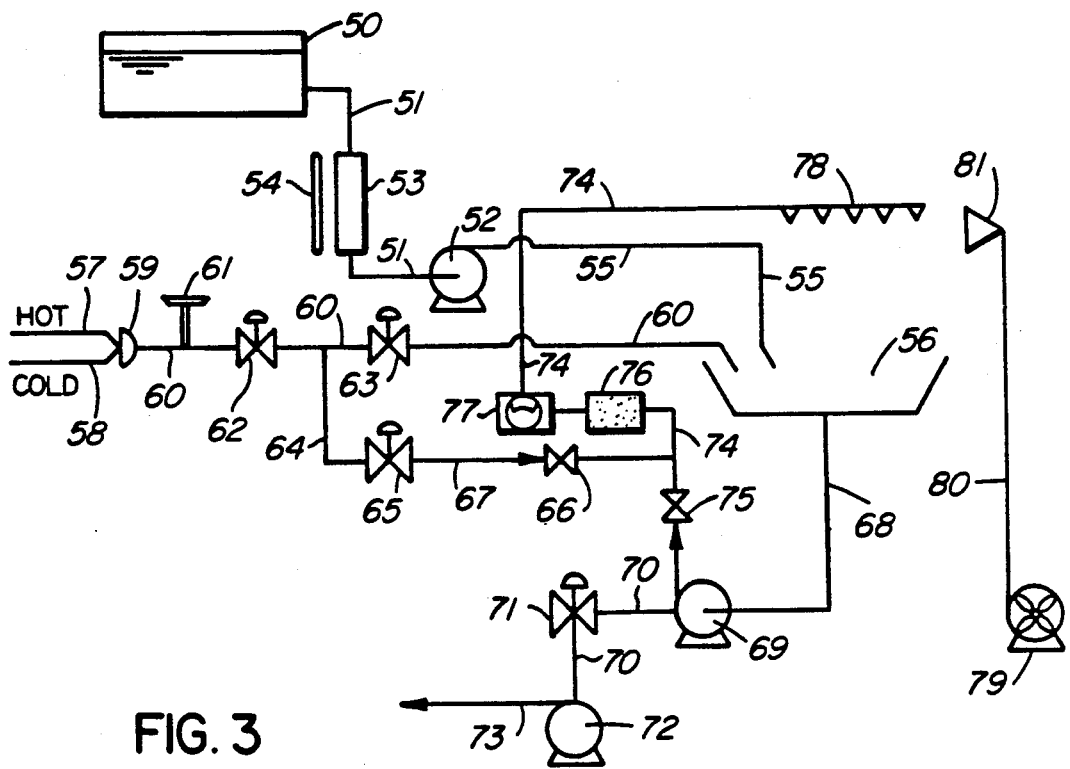
FIG. 3 is a diagram similar to that of FIG. 1 but showing another, embodiment of the device according to the invention.

Turning now to the embodiment of FIG. 3, reference numeral 50 designates a replaceable anti-microbial cartridge containing suitable liquid charge and communicating, via a conduit 51, with an injection pump 52.

The conduit 51 includes, at a point downstream of the cartridge 50, and anti-microbial stand pipe 53 operatively associated with a level transducer 54 for monitoring the level of the antimicrobial liquid still available.

The pressure side of the pump 52, in turn communicates via line 55 with a sump/recirculation tank 56 located inside the apparatus.

Hot and cold water enters, through lines 57, 58, respectively a mixing valve 59 and then continues via line 60, provided with a temperature sensor 61, a metering valve 62 and a control valve 63 to the recirculation tank 56.

Between the valves 62, 63, the line 60 branches to a rinse water conduit 64 provided with a rinse water injection valve 65 and with a check valve 66 to eventually communicate with a line 74 which will be further described later.

The recirculation tank 56 has an outlet at the bottom thereof, which communicates, via a recirculating conduit 68 with the suction side of a recirculation pump 69. The pressure side of the pump 69 branches into two lines; a drain line 70 provided with a drain valve 71, with a disposal pump 72 and thence through a waste conduit 73 to drain.

The second branch of the pressure side of the pump 69 is connected to the already mentioned line 74 provided, respectively, with a check valve 75, a strainer 76 and a pulsator valve 77 and thence to a scrub rinse manifold 78 disposed inside the module 37.

Figure 4:
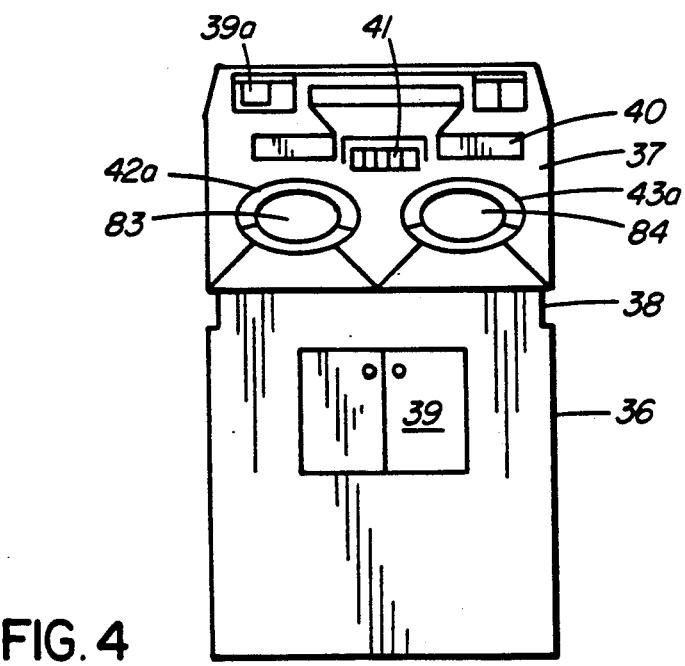
FIG. 4 is a simplified, diagrammatic representation of a front view of the upper part of a modified embodiment of the device shown in FIG. 2.

Reference number 79 designates a fan connected to an air conduit 80 the downstream end of which is provided with an air curtain assembly 81 which, in the embodiment shown, is comprised of a pair of sets of air nozzles, each set being disposed in an oval nozzle ring 42a 43a about a horizontally elongated oval opening 83, 84 in the front of the housing of the device (FIG. 4).

In operation, of the device of FIGS. 1 and 2 or 4, the user actuates the height adjustment switch 41 to bring the ports 29, 30 (or 83, 84) to the elevation most convenient for the particular user. This is done by actuating appropriate switch pad 41 in the front of the device. The ports 29 and 30 are provided with sensing means which are not shown in the drawings and which activate the operating cycle of the device upon inserting of the hands into the ports 29, 30. It should be noted that by now fresh water had been supplied to tank 16 through line 20 and heated to a predetermined temperature, using a suitable heating device not shown. The cartridge 10 is in place and the recirculation tank 19 is also full and mixed with appropriate small volume of the anti-microbial substance coming from cartridge 10. Upon the inserting of hands into the ports 29, 30, the control system of the apparatus opens valve 24 to communicate the tank 19 with pump 28. Valve 26 is activated to allow the flow of the microbe free cleansing substance to the manifolds 24. The vibrating motor 32 is activated to impart radially inward vibrations to the manifolds 27. With the hands disposed between the manifolds 27 (only two manifolds shown in FIG. 2 and those two being only one of a number disposed in one of the ports 29-30) is collected in the collector sump 31. The pump 34 is now operative and the valve 35 is in a mode whereby the line 33 communicates with the recirculation tank 19 to bring the spent scrubbing liquid back into the tank 19 and from there, through line 25, pump 28 and valve 26 back to the manifolds 27.

Upon a predetermined time period, the rinse mode is activated. The valve 35 is open to connect both branches of the line 33 with the drain line 33a to empty not only the pan 31 but also the tank 19. When the tank 19 is empty, the valve 35 leaves only the right hand side of line 33 as viewed in FIG. 1 connected to the drain 33a. During the rinse operation, the valve 24 is actuated to close line 25 and open line 23. The water from pre-heat tank 16 now flows through line 23, valve 24 and pump 28 through valve 26 and into the manifolds 27, becoming collected in pan 31 and from there via line 33 and pump 34, valve 35 to the drain 33a. In order to refill tank 19 before the rinsing cycle is completed, a timer, not shown, activates pump 22 to force the next dosage of pre-heated water 16 into circulation tank 19. Then, the metering pump 12 is activated to deliver, through line 13 and 17, a small, metered volume of anti-microbial substance into the recirculation tank 19. When the predetermined amount has been delivered, the valve 18 is closed. Valve 14 normally stays in a position allowing flow from branch 13 to branch 17. Only exceptionally, when required, a small amount may be administered to the pre-heat tank 16. Thus, before the rinse cycle is completed, the tank 19 is filled with a fresh mixture for the next cycle. The next person using the device then simply starts the entire procedure again, as soon as the preceding rinse cycle is finished.

The control circuitry of the entire device is not shown as a number of different arrangements which in themselves do not form a part of the invention as they are known and consist of commercially available units. The metered volume of anti-microbial substance is used only for one cycle and then drained. Accordingly, a fresh substance is available for each cycle and in a reduced amount.

In a readily conceivable modification of the operative sequence, the operation may start with first filling the recirculation tank 19, followed by administration of a small volume of the anti-microbial substance etc.

In operation of the device diagrammatically shown in FIGS. 3 and 4, the anti-microbial cartridge which is a five or eight liter flexible pouch containing anti-microbial concentrate, is placed into a drawer at 50. The concentrate flows through the upstanding pipe 53. The pipe 53 is designed to contain adequate volume of the concentrate for ten scrubs. When the sensor 54 senses "10" as being empty, a readout (not shown) advises the user that ten scrubs remain and that a new cartridge is required at 50.

The mixer valve 59, governed by thermo-sensor 61, maintains the temperature of water in line 60 at a temperature of about 90°-110° F. If the water does not have the predetermined temperature, the sensor 61 causes the shutdown of the operation and flushing water out of the system.

When a predetermined water temperature is present, the water mixture flows via line 60 into the sump/recirculation tank 56 together with a metered volume of the antiseptic mixture coming from line 55 and from there, being drawn by the pump 69, via line 74, to the strainer 76 which removes any particles having the size in excess of 100 microns, to a the pulsating valve 77. The pulsating valve communicates with the scrub rinse manifold 78 such that pulsations are generated in the manifold 78 in a rotating fashion around the hands and forearms of the user. The manifold 78 contains a plurality of outlet nozzles surrounding the hands and forearms. It can be thus seen that the lines 68 and 74 combine to form a recirculation conduit capable of circulating the mixture from the basin 56, through elements described, back to the basin 56.

When it is desired to stop the operation and flush the system, the valve 75 is closed and valve 71 open allowing the pump 72 to drain the tank 56. while fresh water from line 67 flushes the strainer 76, pulsating valve 77 and the downstream section 74, 78 of the system, down to the sump 56.

When the scrub is finished, the fan 79 is activated to subject the forearms and hands to a strong stream of pressurized air, by way of an air curtain at the oval openings in the housing, to blow off virtually all of the liquid on the surface of the forearms and hands of the user, back into the sump 56 for further use or for draining, depending upon the instant setup of the device.

The timing of the operation is as follows: At the outset, the user adjusts the level of the ports 83, 84 by pressing the height adjustment keypad 41.

This results in the fill injection valve 62, the disposal valve 71 and the disposal pump 72 being all turned on (open). In such state, the fresh water mixture is delivered from the mixing valve 59, via basin 56 to drain downstream of the pump 72. If the temperature sensed at sensor 96 does not reach a value of about 90° F. to about 110° F. within a predetermined period (time zero), the system reverses the operation of the elements 62, 71 and 72 and shuts down the entire operation.

Assuming that the predetermined temperature range is reached within the prescribed period of time, at time 0 (zero), the disposal valve 71 and the disposal pump 72 are both turned off. At the same time, the chemical antimicrobial injection pump 52 is activated to deliver a predetermined batch of the chemical to the basing 56. Thus, fresh water mixture and the antimicrobial substance are both delivered to the basin 56.

Fifteen seconds later (time 15), the pump 52 and the fill injection valve 62 are both turned off. At the same time, the display readout (not specifically shown in FIGS. 2 or 5) "Insert Arms" is activated at 39a (FIG. 4)

The inserting of arms in the device triggers, through a sensor not shown, time 0 (zero) of the scrubbing cycle.

At this time, the recirculation pump 69 and the pulsator valve 77 are both turned on with the result that a pulsating stream of water/chemical mixture is delivered via the line 74 and through a plurality of nozzles of the spray header 78. As mentioned, it is preferred that the pulsating of the spray be provided such that a wave of high pressure pulse travels around the arms of the user by sequential pulse generation at respective nozzles surrounding the inserted arms.

At time 75, i.e. 75 seconds after the inserting of the arms, the recirculation pump 69 is turned off, while the rinse injection valve 65, the disposal valve 71 and the disposal pump 72 are all turned on. This results in rinsing of the inserted arms. At the same time the basin 56 is drained.

At time 90, 90 seconds after the inserting of the arms, the rinse injection valve 65 and the pulsator valve 77 are both turned off.

Following a further delay, the disposal valve 71 and the disposal pump 72 are turned off at time 110 sec and 125 sec., respectively.

It will be appreciated that many modifications of the arrangement disclosed may exist. For instance, the branch 23 could conceivably be provided in line 21 just downstream of pump 22. This and many other modifications, however, would not depart from the scope of the present invention. The indicated possibility of replacement of circular arm ports with horizontally elongated ones is another one of many modifications departing from what has been described but still staying within the scope of the invention. Accordingly, I wish to protect by letters patent which may issue on this application all such embodiments as fairly and properly fall within the scope of my contribution to the art.

I claim:

1. Hand and forearm cleansing device comprising, in combination:

a) cleansing mixture preparation means;

b) an elongated cleansing compartment for washing and rinsing forearms and hands of a person;

c) cleansing mixture spray means disposed in said cleansing compartment;

(1) said cleansing mixture preparation means includes a recirculation means which includes:

(A) catch basin means disposed in said cleansing compartment and disposed in a hydraulic communication with a recirculation conduit having downstream end connected to a recirculation tank, said recirculation conduit including a recirculation pump for drawing liquid from said catch basin means;

(B) water supply means hydraulically connected with the catch basin means for filling the catch basin with a predetermined volume of water;

(C) antimicrobial substance supply means hydraulically connected with the catch basin means for supplying to the basin a predetermined volume of an antimicrobial substance;

(D) drain means adapted to selectively hydraulically connect the catch basin means with a drain;

d) conduit means hydraulically communicating said cleansing mixture preparation means with said spray means;

e) height adjustment power means for selectively modifying a vertical distance between said cleansing compartment and the standing ground of the person;

whereby the substance disposed within the basin can be selectively recirculated to or drained from the basin.

2. The device of claim 1, wherein the cleansing mixture preparation means is included in a stationary first module and the cleansing compartment is included in a second module, said height adjustment power means being a device for raising and lowering said second module relative to said first module.

3. The device of claim 1, wherein said cleansing compartment includes two hand/arm ports each having a periphery; each port being provided with a plurality of pressurized air discharge nozzles disposed inwardly of the periphery, said plurality of discharge nozzles being in a pneumatic communication with a source of pressurized, cleansed, generally microbe free air.

4. The device of claim 3, wherein each port is a horizontally elongated oval port and wherein said discharge nozzles are disposed in a horizontally elongated oval pattern, one pattern for each port, each said pattern generally corresponding to the oval configuration of the respective port.

* * * * *